United States Patent [19]

Honkura et al.

[11] Patent Number: 5,678,998
[45] Date of Patent: Oct. 21, 1997

[54] DENTAL MAGNETIC ATTACHMENT

[75] Inventors: Yoshinobu Honkura, Chita-gun; Lei Tian, Tokai; Hideki Fujii, Chita-gun; Kazuo Arai, Tokai; Yoshinobu Tanaka, Nisshin, all of Japan

[73] Assignee: Aichi Steel Works, Ltd., Tokai, Japan

[21] Appl. No.: 530,860

[22] Filed: Sep. 20, 1995

[51] Int. Cl.$^6$ ............................................. A61C 13/235
[52] U.S. Cl. ............................................................ 433/189
[58] Field of Search ................................................ 433/189

[56] References Cited

U.S. PATENT DOCUMENTS

| | | | |
|---|---|---|---|
| 4,508,507 | 4/1985 | Jackson | 433/189 |
| 4,626,213 | 12/1986 | Shiner et al. | 433/189 |
| 4,815,975 | 3/1989 | Garrel et al. | 433/189 |
| 4,857,873 | 8/1989 | Gillings | 433/189 |
| 5,013,243 | 5/1991 | Tanaka et al. | 433/189 |

FOREIGN PATENT DOCUMENTS

| | | |
|---|---|---|
| 0 387 350 | 9/1990 | European Pat. Off. . |
| 1-303145 | 12/1989 | Japan . |

*Primary Examiner*—Cary E. O'Connor
*Attorney, Agent, or Firm*—Jacobson, Price, Holman & Stern, PLLC

[57] ABSTRACT

A dental magnetic attachment embedded in the denture base so as to face a soft magnetic keeper embedded in the top of the root surface comprising a magnet body with a magnet cover sandwiched by a pair of yoke plates and have its magnetic pole to face the yoke plates, the magnet cover made of corrosion resistant non-magnetic material covering lateral face of the magnet body, the pair of yoke plates made of corrosion resistant soft magnetic material, the keeper made of corrosion resistant soft magnetic material, in condition that the yoke plates and the magnet cover are welded together.

9 Claims, 8 Drawing Sheets

5,678,998

DENTAL MAGNETIC ATTACHMENT

BACKGROUND OF THE INVENTION

1. Field of the Invention

The present invention relates to a dental magnetic attachment which stabilizes a denture on tooth roots.

2. Description of the Related Art

Various types of dental attachment utilizing magnetic attraction as shown in FIGS. 11, 12, and 13 (Japanese patent application Laid-Open (Kokai) No. 1-303145) has been developed up to date. In FIG. 11, a denture consists of artificial teeth 95 and the denture base 94. The artificial teeth are made of ceramics or plastics, and the denture base is made of plastics and the like. In the denture base dental magnetic attachment is embedded facing to the keeper 93. The keeper 93 is embedded in the top of the root surface 930. The root surface 930 is formed on the top of the tooth root 92. The denture is retained by magnetic attractive force acting between the attachment and the keeper. In FIG. 11, 96 indicates gingiva, 99 indicates a denture placed on upper palate.

A dental magnetic attachment shown in FIGS. 12 and 13 comprises a magnet body 81, a pair of yoke plates 82, a spacer 83, a keeper 93 and a cap 84 to cover periphery of these elements except on the side of the keeper 93. The elements except magnet are welded together on the side of the keeper. The magnet body sandwiched by a pair of yoke plates is placed on the spacer and has its magnetic poles to face the yoke plates. The yoke plates and the keeper are made of corrosion resistant soft magnetic material. The cap and the spacer are made of corrosion resistant non-magnetic material.

Miniaturizing in size is strongly required for dental magnetic attachments so that it can be fit in the denture base having narrow free space of approximately 2 mm in the height. Even miniaturizing small amount of 0.1–0.3 mm in the height brings considerable advantage in design and preparation of dentures.

Other major requirements are strong magnetic attractive force above 500 gf and sufficient corrosion resistance in oral cavity. Magnetic force which intensity is proportional to the magnet size is contradictory to miniaturization of the attachments.

Attachments having the structure mentioned above face difficulty in further miniaturization while keeping enough attractive force with them.

SUMMARY OF THE INVENTION

An object of the invention is to provide a dental magnetic attachment having exceedingly small size, enough corrosion resistance and sufficient attractive force.

A dental magnetic attachment according to the present invention comprises a magnet body with a magnet cover, a pair of yoke plates and a keeper. The magnet body and the magnet cover are fixed together by insertion or resin adhesive. The yoke plates and the magnet cover are welded together. The magnet body with the cover is sandwiched by a pair of yoke plates and has its magnetic poles to face the yoke plates. The material of the yoke plates and the keeper may be the same as those of prior art. The material of the magnet cover may be the same as the cap of prior art.

The Present dental magnetic attachment is embedded in the denture base to face to the keeper. The keeper is embedded in the top of the root surface.

Notable difference between prior art and present invention is the method of sealing of corrosive magnet. In prior art the whole elements including magnet are covered by a cap. On the other hand, present invention the lateral faces of magnet are sealed by the magnet cover as shown in FIG. 1.

A rare-earth permanent magnet, such as Sm-Co magnet or Nd-Fe-B magnet, having a maximum energy product of at least 20 MGOe is recommendably used for the magnet body. A corrosion resistant soft magnetic alloy having saturation magnetic flux density of at least 13000G and permeability of at least 3000 is recommendably used for the yoke plates and the keeper. Suitable material is ferritic stainless steel such as 19Cr-2Mo-Ti steel of 17Cr-2Mo-Ti steel.

The kinds of corrosion resistant non-magnetic material used for magnet cover are SUS316L stainless steel, Ti and its alloys, Pd-Co-Ni alloys, Au and its alloys, and Au-Pd alloy.

The yoke plates and the magnet cover are welded or soldered along periphery of the magnet cover. Laser welding and electron beam welding forms superior joint surface which is good in flatness and narrow in welding width.

It is preferable that the yoke plate 12 has round or inclined face 125 on the upper side opposite to magnet as shown in FIG. 5. It is also preferable that the magnet body and the magnet cover have inclined face 134 on the opposite side to the keeper as shown in FIG. 8. The shape mentioned above causes no deterioration in magnetic attractive force because it does not disturb the flow of magnetic flux. And it enables the volume of the attachment to become small. The shape also provides easy insertion of the attachment to the denture base.

Furthermore it is preferable that the yoke plate have a groove on the outer side. The groove makes strong adhesion of the attachment to the denture base. Namely, the attachment is fixed to the denture base made of resin or the like with adhesive. Resin deterioration is apt to cause trouble that the attachment falls off from the denture base.

However the groove filled with resin holds the attachment mechanically to the denture base. So that it can prevent falling off of attachment from the denture base.

The groove is formed along the outer side of the keeper. The groove can be formed to cover the whole outer side of the yoke plate of a part of it.

Although the invention presented above is described for the case that the keeper is set in the root surface and the attachment in the denture base, the present invention includes the case in which the keeper and the attachment are placed vise versa. In latter case the structure of the attachment is the same as the one described above.

THE PREFERRED EMBODIMENTS OF THE PRESENT INVENTION

Figure 1:
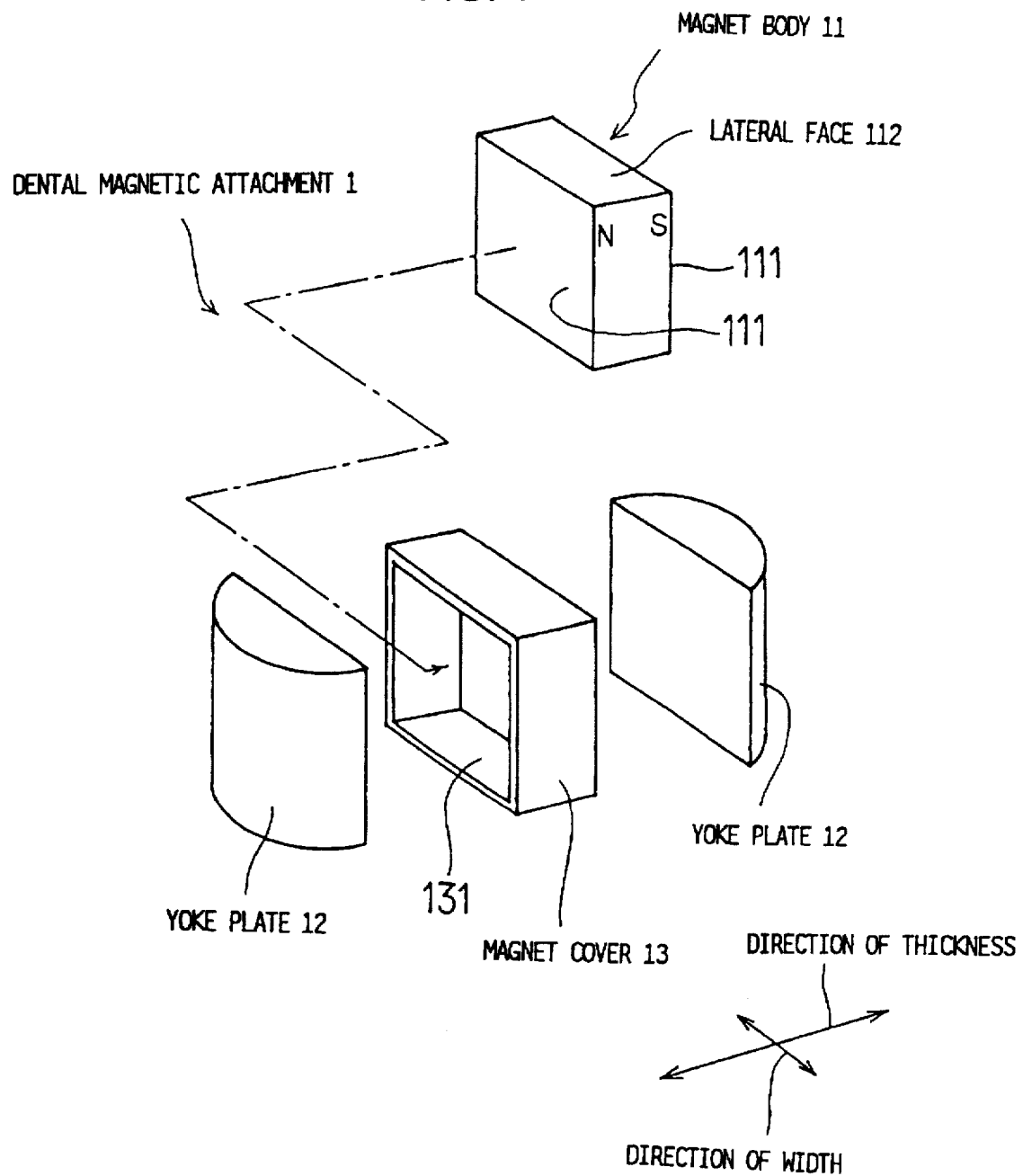
FIG. 1 is an exploded perspective view of the first embodiment of a dental attachment according to the present invention.
Figure 2:
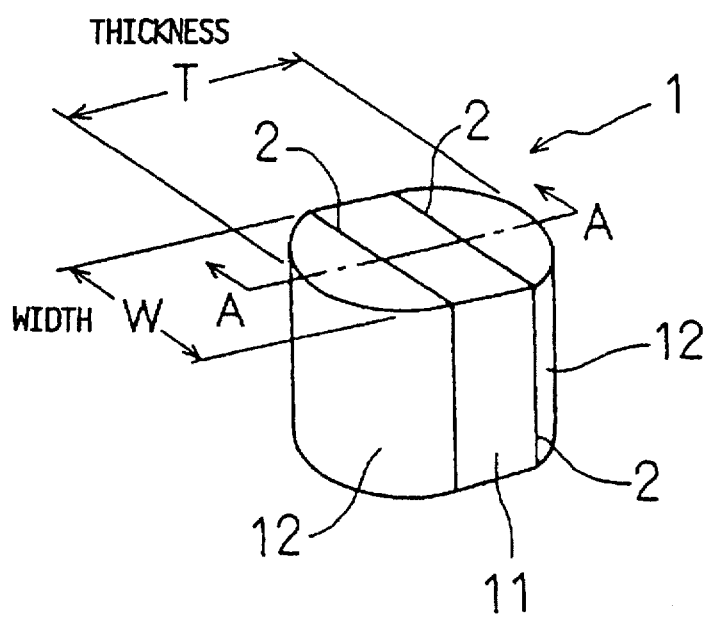
FIG. 2 is a perspective view of the first embodiment of a dental attachment according to the present invention.
Figure 3:
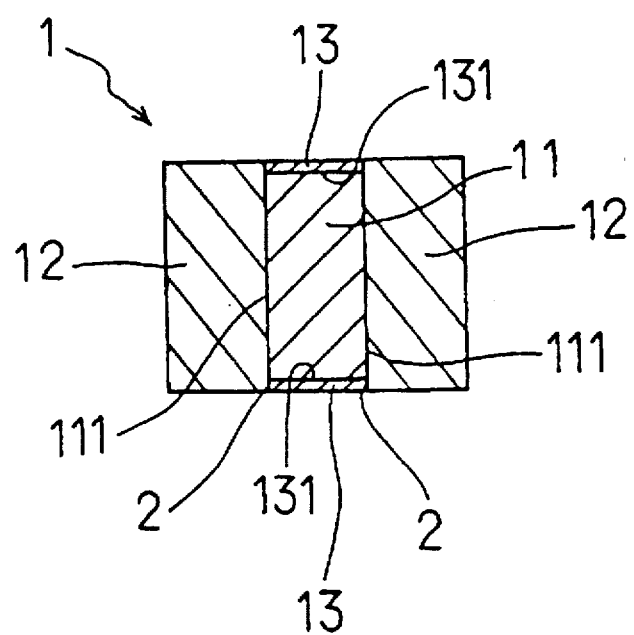
FIG. 3 is a sectional illustration taken along line A—A of FIG. 2.

Three kinds of the embodiments according to the present invention will be described with reference to FIG. 1 to FIG. 9.

The first example, as shown in FIG. 1 to FIG. 4, comprises a magnet body 11 having lateral face 112 with a magnet cover 13, a pair of yoke plates 12 and a keeper 3. The yoke plates and the magnet cover are laser welded together. The magnet body with the cover is sandwiched by a pair of the yoke plates and have its magnetic poles 111 facing the yoke plates. The yoke plates and the keeper are made of 19Cr-2Mo-Ti stainless steel. The magnet cover is made of SUS316L stainless steel.

The magnet body 11 is inserted in the opening 131 of the magnet cover 13. Shape and dimension of the magnet body 11 are as same as those of opening 131. The magnet body 11 and the magnet cover 13 are fixed together by insertion.

The magnet body 11 is a rectangular plate. The shape of magnet cover and its opening is rectangular. Outer side of the yoke plates 12 is round when they are viewed from top of the attachment and flat in opposite sides which face to the magnet.

Figure 5:
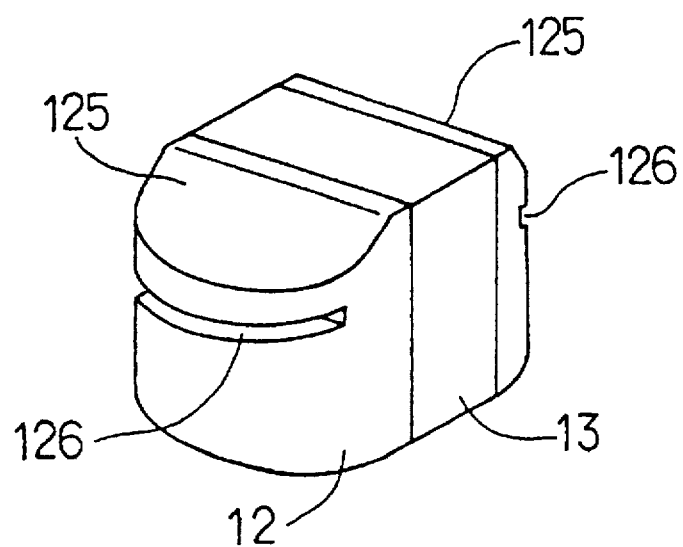
FIG. 5 is perspective view of the second embodiment of a dental attachment according to the present invention.
Figure 6:
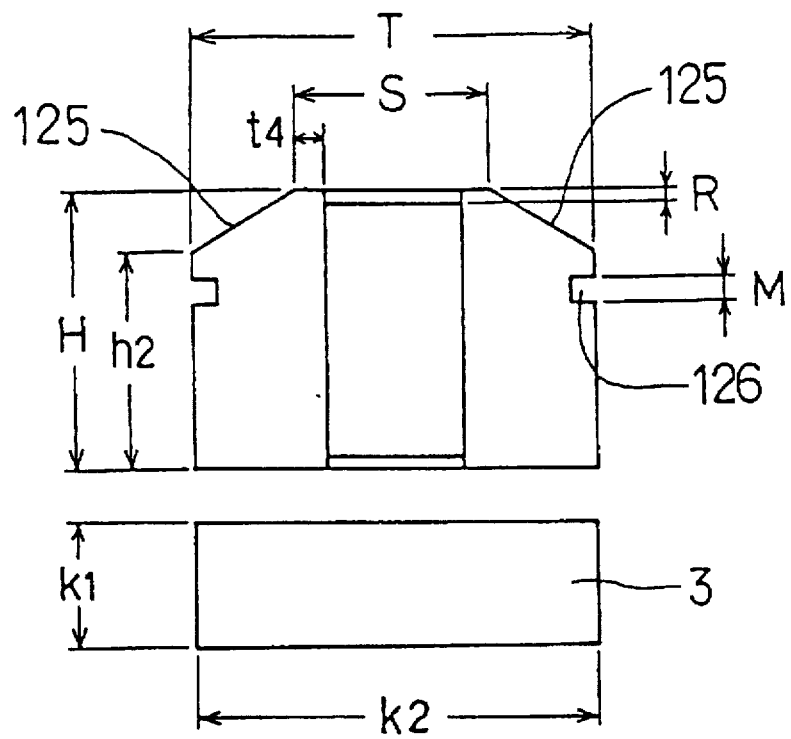
FIG. 6 is a diagram to illustrate the dimension of the second embodiment along the direction of width.
Figure 7:
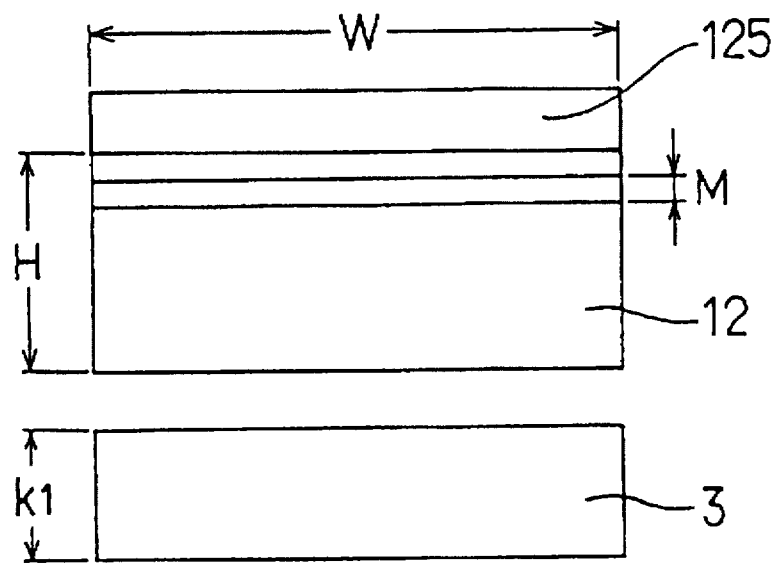
FIG. 7 is a diagram to illustrate the dimension of the second embodiment along the direction of width.

Second example as shown in FIG. 5 to FIG. 7 has yoke plates 12 with inclined faces 125 and grooves 126 on the side opposite to the magnet.

The inclined face 125 is formed on the upper side opposite to the keeper and its inclination is about 30 degrees. The groove 126 formed along the round outer side of the yoke plate has a constant depth. Other specifications are as same as the first example.

Figure 8:
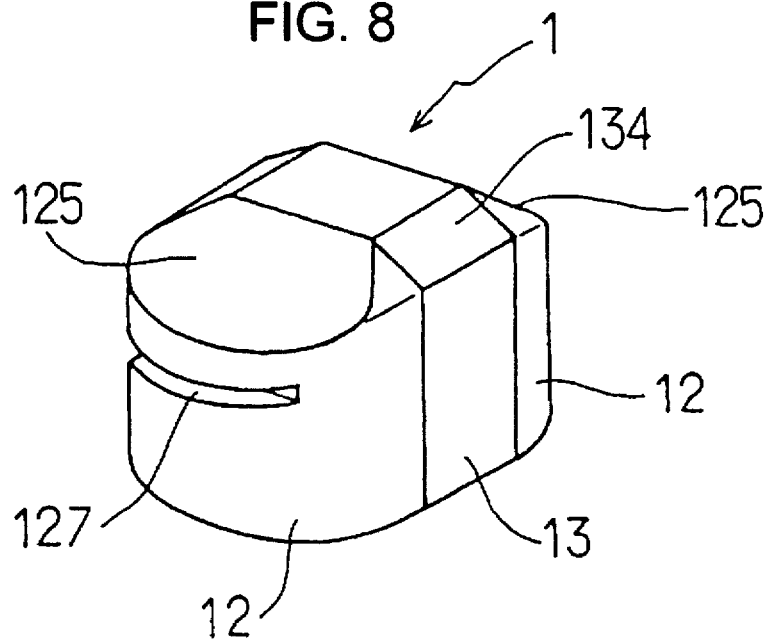
FIG. 8 is a perspective view of the third embodiment of a dental attachment according to the present invention.
Figure 9:
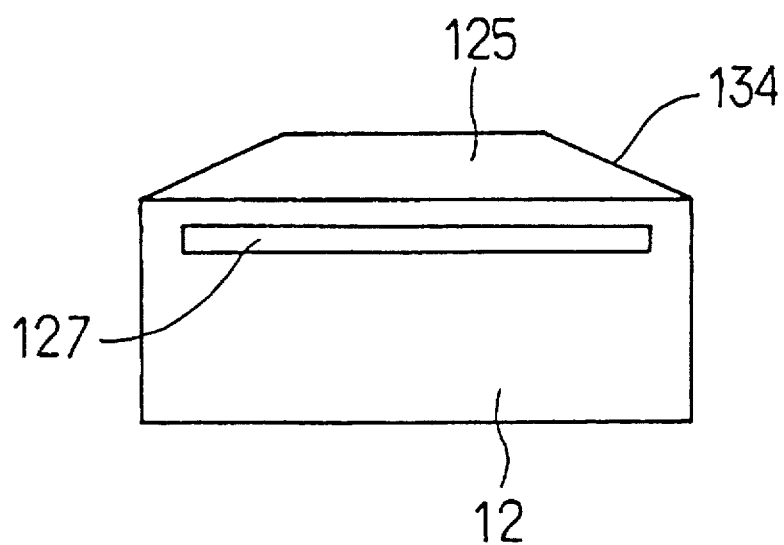
FIG. 9 is a diagram to illustrate the dimension of the third embodiment along the direction of width.

Third example as shown in FIG. 8 and FIG. 9 has a magnet cover 13 with inclined faces 134 on the opposite side to the keeper. Accordingly the magnet body 11 has same inclined face on the same side. Other specifications are as same as the second example.

Now four kinds of dental magnetic attachments, Sample 1, Sample 2, Sample 3 and Sample 4, were produced according to the present invention and the attractive force (gf) and reluctance against falling off (kgf) were measured as shown in table 1 to table 6.

An attachment produced by prior art is also submitted to same measurements as comparison.

The structure of sample 1 corresponds to that of the first embodiment of present invented attachment, sample 2 to the second embodiment, and sample 3 and 4 to the embodiment 3.

The dimension, magnetic properties and the material used for elements of the sample 1 through 4 and a comparative sample are shown in tables 1 to 5. The elements mentioned above are the magnet body, the magnet cover, the yoke plates, the groove and the keeper.

Table 6 shows the dimension, attractive force, reluctance of falling off of assembled attachments.

The dimension of the top side is defined by width and thickness of the top side (the opposite to the keeper) of the attachment.

The width mentioned above means the length of the top face measured along the direction parallel to the magnet pole face, as shown FIG. 1. The thickness mentioned above means the length of the top face measured along the direction normal to the magnet pole face, as shown in FIG. 1.

The dimension of the bottom side is defined by width and thickness of the bottom side (facing to the keeper) of the attachment.

The sample 1 with no inclined face in the upper part has the dimensions of the top side equals to that of bottom side as shown in Table 6. The samples 2, 3, and 4 with inclined face have the dimensions of the top side different from that of bottom side. The dimensions of bottom side of samples 1 through 4 are fixed to the common value. The thickness of the comparative sample is 0.2 mm longer than that of samples of present invention. The maximum height means the height of assembled attachment. The shoulder height means the height from bottom to the lower end of inclined face.

The magnetic attractive force between the attachment and the keeper was measured by an Instron type tensile measuring apparatus. The reluctance of falling off is defined by tensile force as pulling out attachment from the denture base measured by the apparatus mentioned above. The attachments were cemented in resin denture base with adhesive commonly used in prosthetics.

The specifications of the attachments as shown in tables 1 to 5 is described as folows.

Figure 4:
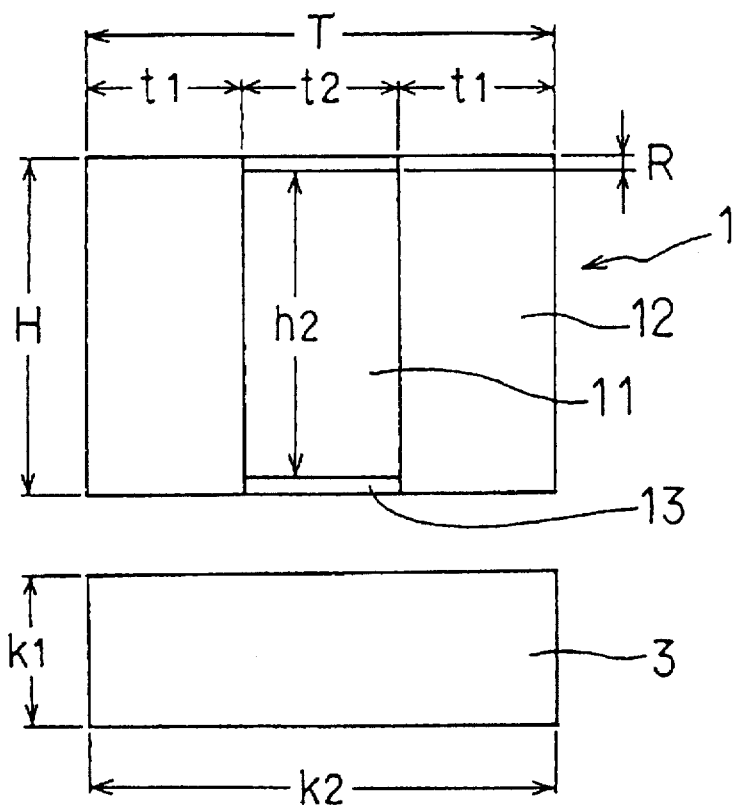
FIG. 4 is a diagram to illustrate the dimension of the first embodiment along the direction of thickness.

At first, the speciication of sample 1 shown in table 1 is described using FIG. 4. The magnet body 11 has the thickness t2 of 1.0 mm, the thickness of material R of 0.1 mm, the width w of 4.2 mm.

The yoke plate 12 has the thickness t1 of 1.0 mm, the height H of 2.1 mm, the width w (see FIG. 7) of 4.2 mm.

The keepers of sample 1 through 4 have the thickness K2 of 3.0 mm, the width of 4.2 mm which are same as that of attachments, and the height K1 of 1.0 mm. The keeper of comparative sample has same width and height of sample 1 through 4, but the thickness of 3.2 mm.

For example 2, 3 and 4 having inclined face, shoulder height h2 defined in FIG. 6 are shown in table 2, 3 and 4. Also, the width, depth and length of the grooves are shown.

Now the results of measurements given in table 6 are described as follows.

The attractive force of sample 1 equal to that of the comparative sample, although sample 1 has smaller size with 3.0 mm, thickness which is 0.2 mm less than that of comparative one. Here the samples have same width of 4.2 mm.

Sample 2 has equal attractive force to the comparative sample although the volume of sample 2 is reduced by inclined face at the upper part of yoke plates. This means that inclined face provides increase of attractive force per unit volume.

Sample 3 also has same level of attractive force in spite of further miniaturization by placing inclined faces in both yoke plates and the magnet body.

Sample 4 has same dimension as sample 3 but Nd-Fe-B magnet higher energy product of 35MGOe is used in it. The Nd-Fe-B magnet increases the attractive force than that of the comparative sample.

Sample 2, 3 and 4 having grooves 126, 127 shows reluctance in falling off from the denture base.

TABLE 1

Dimension of the Elements of Sample 1

| | Dimension (mm) | Magnetic property | Material |
|---|---|---|---|
| magnet body | thickness 1.0, height 1.9, width 4.0 | 32MGOe | $Sm_2Co_{17}$ |
| magnet cover | thickness 1.0, height 2.1, width 4.2, material thickness 0.1 | permeability = 1.02 | SUS316L |
| yoke plate | thickness 1.0, height 2.1, width 4.2 | 1.6T | 19Cr—2Mo—Ti |
| groove | none | — | — |
| keeper | height 1.0 | 1.6T | 19Cr—2Mo—Ti |

TABLE 2

Dimension of the Elements of Sample 2

| | Dimension (mm) | Magnetic property | Material |
|---|---|---|---|
| magnet body | thickness 1.0, height 1.9, width 4.0 | 32MGOe | $Sm_2Co_{17}$ |
| magnet cover | thickness 1.0, height 2.1, width 4.2, material thickness 0.1 | permeability = 1.02 | SUS316L |
| yoke plate | thickness 1.0, height 2.1, shoulder height 1.64, width 4.2 | 1.6T | 19Cr—2Mo—Ti |
| groove | width 0.2, depth 0.2, length 4.2 | — | — |
| keeper | height 1.0 | 1.6T | 19Cr—2Mo—Ti |

TABLE 3

Dimension of the Elements of Sample 3

| | Dimension (mm) | Magnetic property | Material |
|---|---|---|---|
| magnet body | thickness 1.0, height 1.9, shoulder height 1.64, width 4.0 | 32MGOe | $Sm_2CO_{17}$ |
| magnet cover | thickness 1.0, height 2.1, shoulder height 1.64, maximum width 4.2, minimum width 2.4, material thickness 0.1 | permeability = 1.02 | SUS316L |
| yoke plate | thickness 1.0, height 2.1, shoulder height 1.64, maximum width 4.2, minimum width 2.4 | 1.6T | 19Cr—2Mo—Ti |
| groove | width 0.2, depth 0.2, length 2.0 | — | — |

TABLE 3-continued

Dimension of the Elements of Sample 3

| | Dimension (mm) | Magnetic property | Material |
|---|---|---|---|
| keeper | height 1.0 | 1.6T | 19Cr—2Mo—Ti |

TABLE 4

Dimension of the Elements of Sample 4

| | Dimension (mm) | Magnetic property | Material |
|---|---|---|---|
| magnet body | thickness 1.0, height 1.9, shoulder height 1.64, width 4.0 | 25MGOe | $Nd_{14}Fe_{77}B_8$ |
| magnet cover | thickness 1.0, height 2.1, shoulder height 1.64, maximum width 4.2, minimum width 2.4, material thickness 0.1 | permeability = 1.02 | SUS316L |
| yoke plate | thickness 1.0, height 2.1, shoulder height 1.64, maximum width 4.2, minimum width 2.4 | 1.6T | 19Cr—2Mo—Ti |
| groove | width 0.2, depth 0.2, length 2.0 | — | — |
| keeper | height 1.0 | 1.6T | 19Cr—2Mo—Ti |

TABLE 5

Dimension of the Elements of Sample 5

| | Dimension (mm) | Magnetic property | Material |
|---|---|---|---|
| magnet body | thickness 1.0, height 1.9, width 4.0 | 32MGOe | $Sm_2Co_{17}$ |
| yoke plate | thickness 1.0, height 2.0, width 4.0 | 1.6T | 19Cr—2Mo—Ti |
| spacer | thickness 1.0, height 0.1, width 4.0 | permeability = 1.02 | SUS316L |
| cap | periphery of assembled attachment, material thickness 0.1 | permeability = 1.02 | SUS316L |
| keeper | height 1.0 | 1.6T | 19Cr—2Mo—Ti |

TABLE 6

Results of the Measurements

|  |  | sample 1 | sample 2 | sample 3 | sample 4 | comparative sample |
|---|---|---|---|---|---|---|
| dimension of top side (mm) | width | 4.2 | 4.2 | 2.4 | 2.4 | 4.2 |
|  | thickness | 3.0 | 1.4 | 1.4 | 1.4 | 3.2 |
| dimension of bottom side (mm) | width | 4.2 | 4.2 | 4.2 | 4.2 | 4.2 |
|  | thickness | 3.0 | 3.0 | 3.0 | 3.0 | 3.2 |
| maximum height (mm) |  | 2.1 | 2.1 | 2.1 | 2.1 | 2.1 |
| shoulder height (mm) |  | 2.1 | 1.64 | 1.64 | 1.64 | 2.1 |
| attractive force (gf) |  | 628 | 630 | 620 | 645 | 630 |
| reluctance against falling off (kgf) |  | 16 | 27 | 27 | 27 | 16 |

Figure 10A:
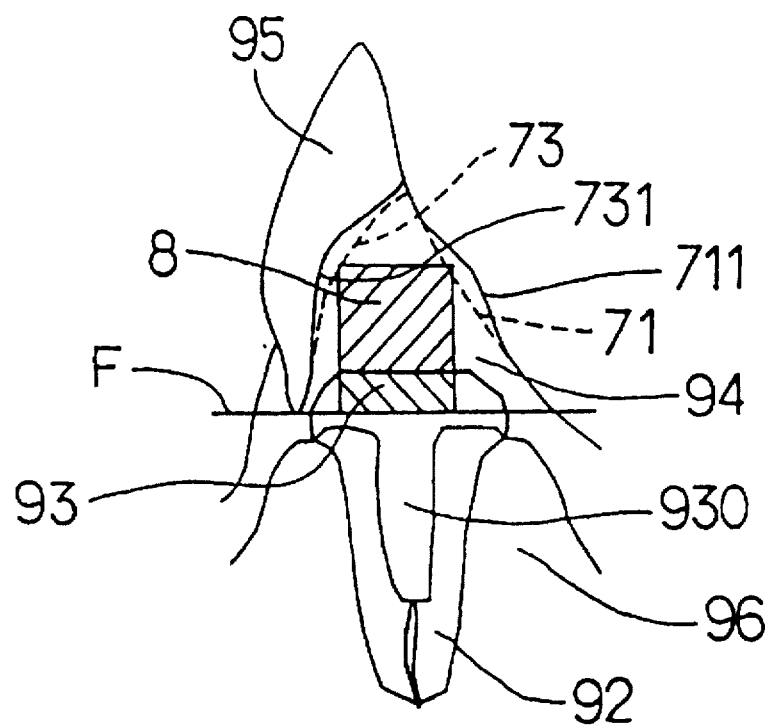
FIG. 10 is a diagram to illustrate the difference between prior art (A) and present invention (B)
Figure 10B:
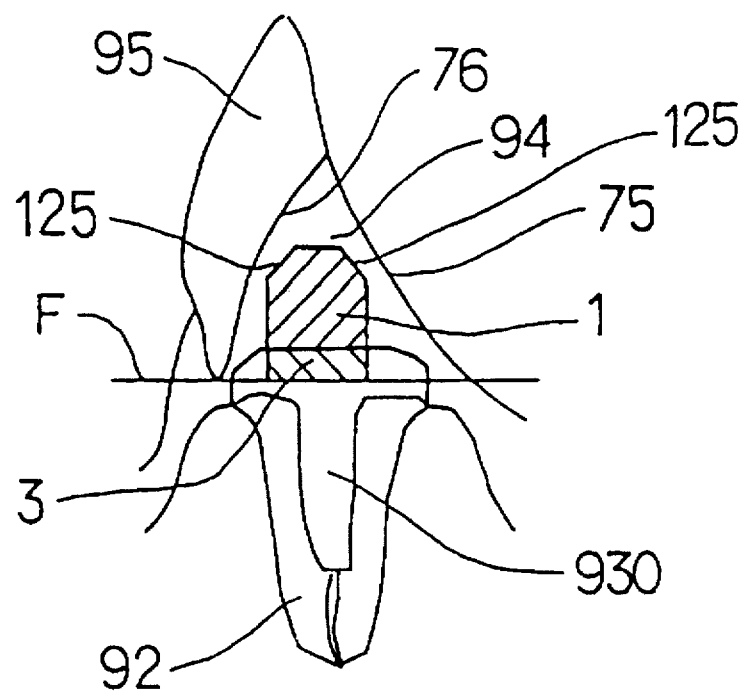
Figure 11:
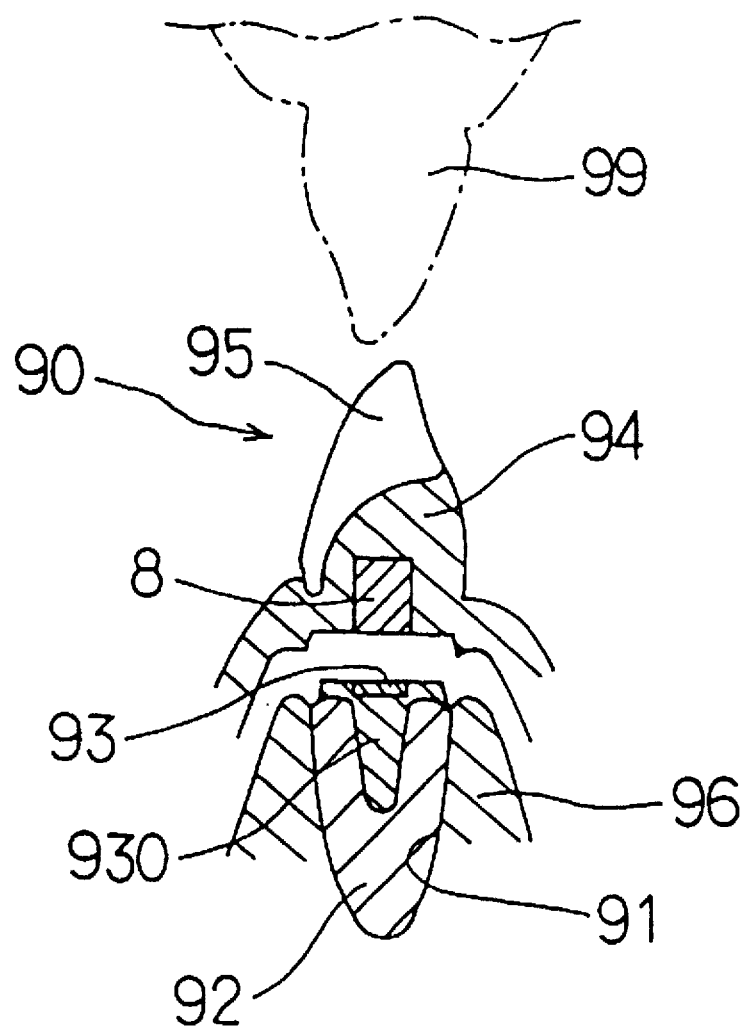
FIG. 11 is an illustration of the denture utilizing prior art.
Figure 12:
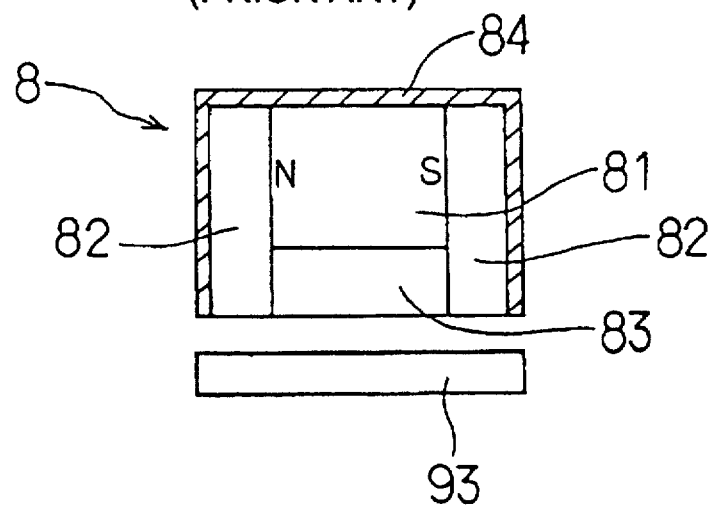
FIG. 12 is an illustration of the dental magnetic attachment by prior art.
Figure 13:
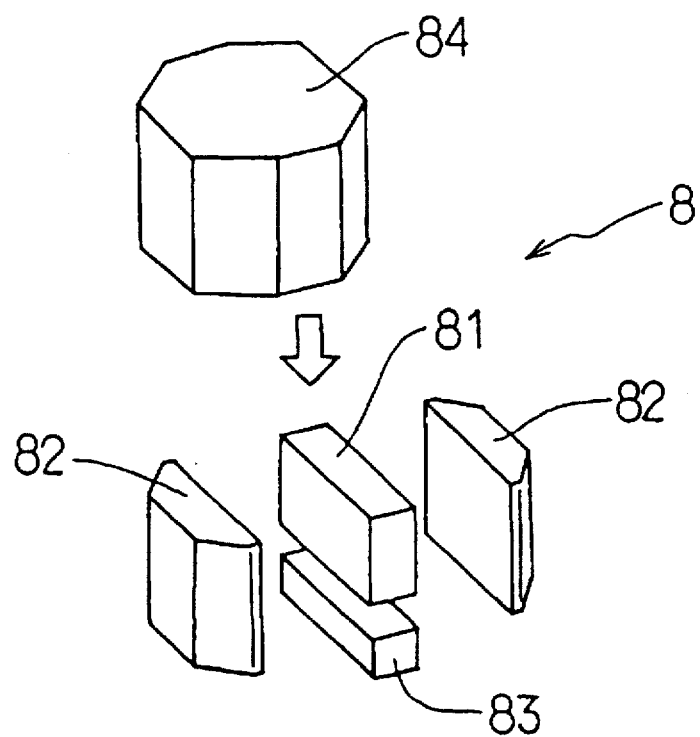
FIG. 13 is an exploded perspective view of the dental magnetic attachment by prior art.

Now the advantage of present invention to prior art in preparing denture is described using comparative sample in FIG. 10 (A) and sample 3 in FIG. 10 (B).

As shown in FIG. 10 (A), denture should be formed along the dotted line 71 and 73. However comparative sample is large in the height and the thickness so that the denture base has to be formed along the line 711, and artificial tooth 95 along the line 731. The line 711 causes unpleasant feeling of having alien substance in oral cavity. The line 731 causes mechanical weakness of artificial tooth.

One the other hand sample 3 having smaller size in the height and the thickness with the inclined face enables ideal line of 75 and 76. Particularly the inclined faces 125 contribute to form the lines as FIG. 10 (B) reveals. The line 75 causes no ill feeling to tongue. The line 76 ensures sufficient mechanical strength to artificial tooth.

As conclusion, present invention provides significant advantages is preparing dentures.

What is claimed is:

1. A dental magnetic attachment embedded in a denture base so as to face a soft magnetic keeper embedded in a top of a root surface comprising:

a magnet body with a magnet cover sandwiched between a pair of yoke plates and having its magnetic poles facing said yoke plates, said magnet cover being made of corrosion resistant non-magnetic material covering a lateral face of said magnet body, said pair of yoke plates being made of corrosion resistant soft magnetic material, and a keeper made of corrosion resistant soft magnetic material welded together with said pair of yoke plates and said magnet cover, said magnet body and said magnet cover having an inclined face on opposite sides of said keeper.

2. The dental magnetic attachment as set forth in claim 1, wherein said pair of yoke plates have a round face on an upper side opposite to said magnet body.

3. The dental magnetic attachment as set forth in claim 2, wherein said pair of yoke plates have a groove on an outer side of each.

4. The dental magnetic attachment as set forth in claim 1, wherein said pair of yoke plates have an inclined face on an upper side opposite to said magnet body.

5. A dental magnetic attachment embedded in a denture base to be magnetically attached to a soft magnetic keeper embedded in a top of a root surface comprising:

a pair of yoke plates made of corrosion resistant soft magnetic material, spaced from each other, to be magnetically attached to said soft magnetic keeper, a magnet body sandwiched between said pair of yoke plates and having its magnetic poles facing said yoke plates, and a magnet cover made of corrosion resistant non-magnetic material covering a lateral surface of said magnet body and welded to said yoke plates to cover the entire surface of said magnet body with said magnet cover and said pair of yoke plates.

6. The dental magnetic attachment as set forth in claim 5, wherein said pair of yoke plates have a round face on an upper side opposite to said magnet body.

7. The dental magnetic attachment as set forth in claim 6, wherein said pair of yoke plates have a groove on the outer side of each.

8. The dental magnetic attachment as set forth in claim 6, wherein said magnet body and said magnet cover have an inclined face on opposite sides of said keeper.

9. The dental magnetic attachment as set forth in claim 5, wherein said pair of yoke plates have an inclined face on an upper side opposite to said magnet body.

* * * * *